United States Patent [19]
Lane et al.

[11] Patent Number: 6,002,994
[45] Date of Patent: Dec. 14, 1999

[54] METHOD OF USER MONITORING OF PHYSIOLOGICAL AND NON-PHYSIOLOGICAL MEASUREMENTS

[76] Inventors: Stephen S. Lane, 4915 River Rd., Bethesda, Md. 20816; Christopher Chadbourne, 3107 N. 18th St., Arlington, Va. 22201; William T. Buller, 5039 Bradley Blvd. #3, Bethesda, Md. 20816; Sarah A. Steiger, 736 Vermont St., Arlington, Va. 22094

[21] Appl. No.: 08/302,434

[22] Filed: Sep. 9, 1994

[51] Int. Cl.⁶ .................................................. G01B 17/00
[52] U.S. Cl. ............................................................ 702/188
[58] Field of Search ................................ 702/1, 19, 187, 702/188, 130, 131, 138, 45, 46, 47

[56] References Cited

U.S. PATENT DOCUMENTS

| | | | |
|---|---|---|---|
| 4,529,874 | 7/1985 | Zierhut | 250/221 |
| 4,803,625 | 2/1989 | Fu et al. | 364/413.03 |
| 5,410,471 | 4/1995 | Alyfuku et al. | 364/413.02 |

*Primary Examiner*—James P. Trammell
*Attorney, Agent, or Firm*—Rodger H. Flagg

[57] ABSTRACT

A method for monitoring the activities of a user within a selected environment, which comprises monitoring and reporting the condition of a user in a selected environment, monitoring the time, frequency and duration of use of each of a plurality of selected elements, selected from a plurality of physiological measurements of the user and a plurality of non-physiological measurements from the selected environment, a repeating hub for receiving data from each of the selected elements, transmitting the data from the repeating hub to a central processing unit, analyzing the data received by the central processing unit to establish a pattern of user behavior and normal-use parameters for each of the plurality of selected elements, and signaling beyond the selected environment when at least one selected element exceeds the normal use parameters being monitored.

22 Claims, 14 Drawing Sheets

|  | State on opening | |
|---|---|---|
| State on closing | No one inside | Some one inside |
| No one inside | Look in | Entry |
| Some one inside | Exit | Look out |

Figure 20

METHOD OF USER MONITORING OF PHYSIOLOGICAL AND NON-PHYSIOLOGICAL MEASUREMENTS

BACKGROUND OF THE INVENTION

The present invention relates to monitoring the activities one or more users in a selected environment to determine if assistance is needed.

Prior art devices are known to monitor a selected person, and to signal an alarm if that person leaves a pre-determined area. Such devices are used to monitor an individual under "house arrest".

Other apparatus is known to locate lost or missing children. Various security devices are also known, such as burglar alarms, smoke and fire alarms, flood alarms, etc.

One form of burglar alarm, known as-motion detector alarms, are used to sound an alarm where motion occurs in a secured environment.

SUMMARY OF THE INVENTION

The present invention is directed to a method of user monitoring, for monitoring and reporting the condition of a user in a selected environment. A monitoring means is used for monitoring the time, frequency, and duration of use of each of a plurality of selected elements. The selected elements are selected from physiological measurements of the user, and from non-physiological measurements from the selected environment. A reporting means is used for transmitting the data from each of the monitoring means to a repeating hub, or directly to a central processing unit. A transmitting means is used for transmitting the data from the each of the monitoring means, or from a repeating hub, to a central processing unit. An analyzing means is used for analyzing the data received by the central processing unit to establish a pattern of user behavior and normal-use parameters for each of the plurality of selected elements. The analyzing means is also used to analyze data from several selected signaling means, to analyze a combination of user behavior and normal-use parameters. A signaling means is used for signaling beyond the selected environment when at least one selected element, or combination of elements, deviates from the normal-use parameters being monitored. The data received from the signaling means may be reviewed by others at a remote location, or the data may be retained at the central processing unit (CPU) as an ongoing record of user behavior, for later review by others.

DESCRIPTION OF THE DRAWINGS

The above mentioned and other features and objects of this invention and the manner of attaining them will become more apparent and the invention itself will be best understood by reference to the following description of the invention taken in conjunction with the accompanying drawings, wherein:

FIG. 20 is a truth table showing the status of the door monitor.

DESCRIPTION OF THE PREFERRED EMBODIMENT

Figure 1:
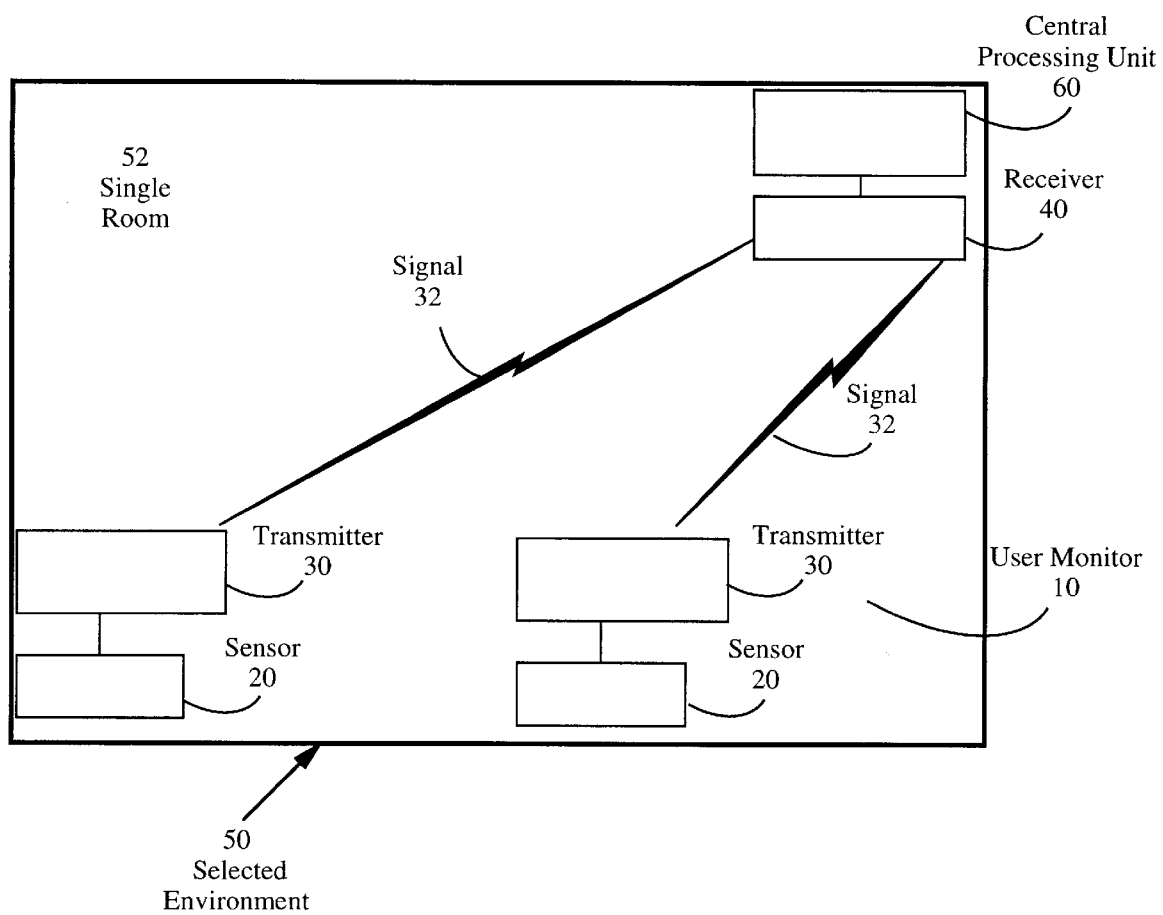
FIG. 1 is a diagram showing the sensors, transmitters and central processing unit located within the selected environment.

As shown in FIG. 1, the user monitor 10 comprises a plurality of sensors 20, each sensor 20 preferably having a single channel transmitter 30 for sending a signal to a multichannel receiver 40 located within the selected environment 50 to be monitored. The multichannel receiver 40 sends the data received from each of the plurality of sensors 20 to an internal central processing unit 60.

The central processing unit 60 may include Analog-to-Digital converters (A/D) to change the analog input from the sensors 20 to digital data. Where digital data is sent directly to the CPU from the sensors 20, no D/A converters are needed. A multichannel receiver may be used, as shown in FIG. 1, to receive input from the plurality of sensors 20 used in the selected environment 50.

The signals 32 from the sensors 20 may be radio waves, ultrasonic waves, infrared energy waves, or signals 32 sent over a suitable hard wire link, such as fiber optic cables, telephone lines, cable television lines, coaxial cable lines, etc. When hard wire links are used, the signals 32 may pass through existing wires located within the selected environment 50, or the signals 32 may be routed through wires especially strung within the selected environment 50 for this purpose. The wires may carry electric power, or may be in the form of coaxial cable to transmit television signals, etc.

The signals 32 from the transmitter 30 are preferably heterodyned to a frequency away from the frequency employed by the original user of the wire.

As shown in FIG. 1, the selected environment 50 may be a single room 52 in a dwelling. The user monitor 10 shown in FIG. 1 is suitable for a detached selected environment 50 far away from other non-interactive user monitors 10, where transmission of data from the sensors to an external CPU 60 might be corrupted by interference from power lines, radio stations, electromagnetic storms, etc. The user monitor 10 shown in FIG. 1 utilizes an internal CPU for data processing and data storage for later retrieval. Retrieval of data from the internal CPU may be over telephone lines to a remote modem or human listener, or from a cathode ray tube screen located at the CPU 60.

Figure 2:
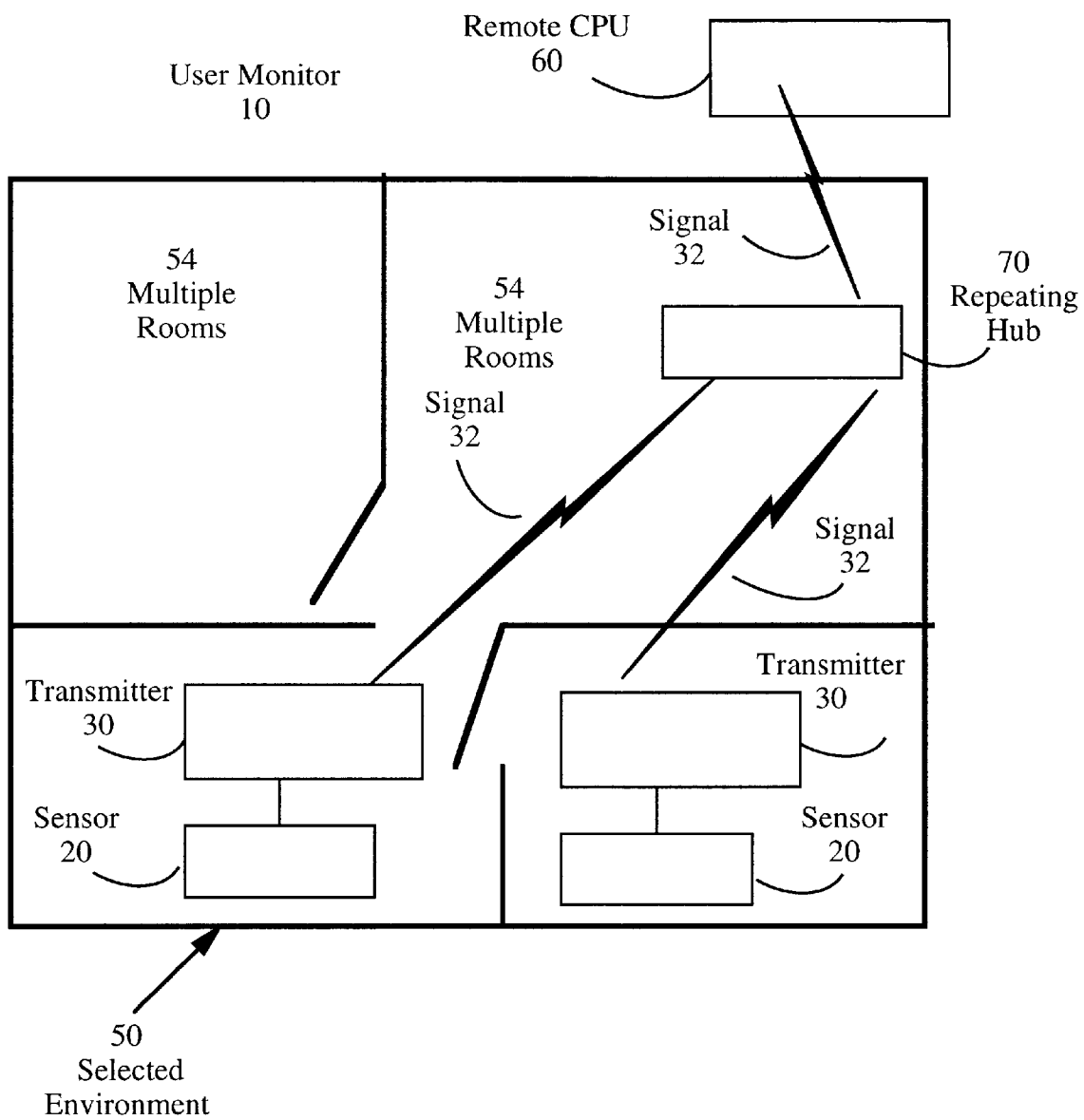
FIG. 2 is a diagram showing the sensors, transmitters, and a repeating hub for transmitting data to a central processing unit remotely located beyond the selected environment.

As shown in FIG. 2 the selected environment 50 may also comprise multiple rooms 54 in the selected environment 50. A number of selected environments 50 may be simultaneously monitored by a remote source, enabling the remote source to monitor a plurality of single rooms 52, or multiple rooms 54, including a plurality of detached homes, apartment units, nursing home units, hospital units, office units, etc.

As shown in FIG. 2, the non-interactive user monitor 10 may use a repeating hub 70 to receive and store the signals 32 from a plurality of transmitters 30 until the repeating hub 70 is interrogated by a remote CPU. A small CPU, or computer chip, may be incorporated within the repeating hub 70 for this purpose. The remote CPU 60 may transmit and receive data from the repeating hub 70 by any known means, so long as the known means does not interfere with the transmission of data from the sensors 20 to the repeating hub 70.

The remote CPU preferably queries the selected repeating hub 70 by a suitable signal. The repeating hub 70 will then transmit all its current data to the remote CPU 60. The repeating hub 70 may transmit data received from the sensors 20 in serial fashion in a pre-arranged sequence; or the data may be transferred to the remote CPU in parallel fashion, with each sensor's 20 data on a separate radio frequency, ultrasonic, infrared or hard wired link. Parallel transfer of data allows a higher data rate at the expense of requiring more transmitters 30, receivers 40, and I/O channels.

The transfer of data by either serial or parallel fashion, allows the monitoring of several hundred selected environments simultaneously by a single remote CPU, which significantly reduces the cost of the non-interactive user monitor 10.

Figure 3:
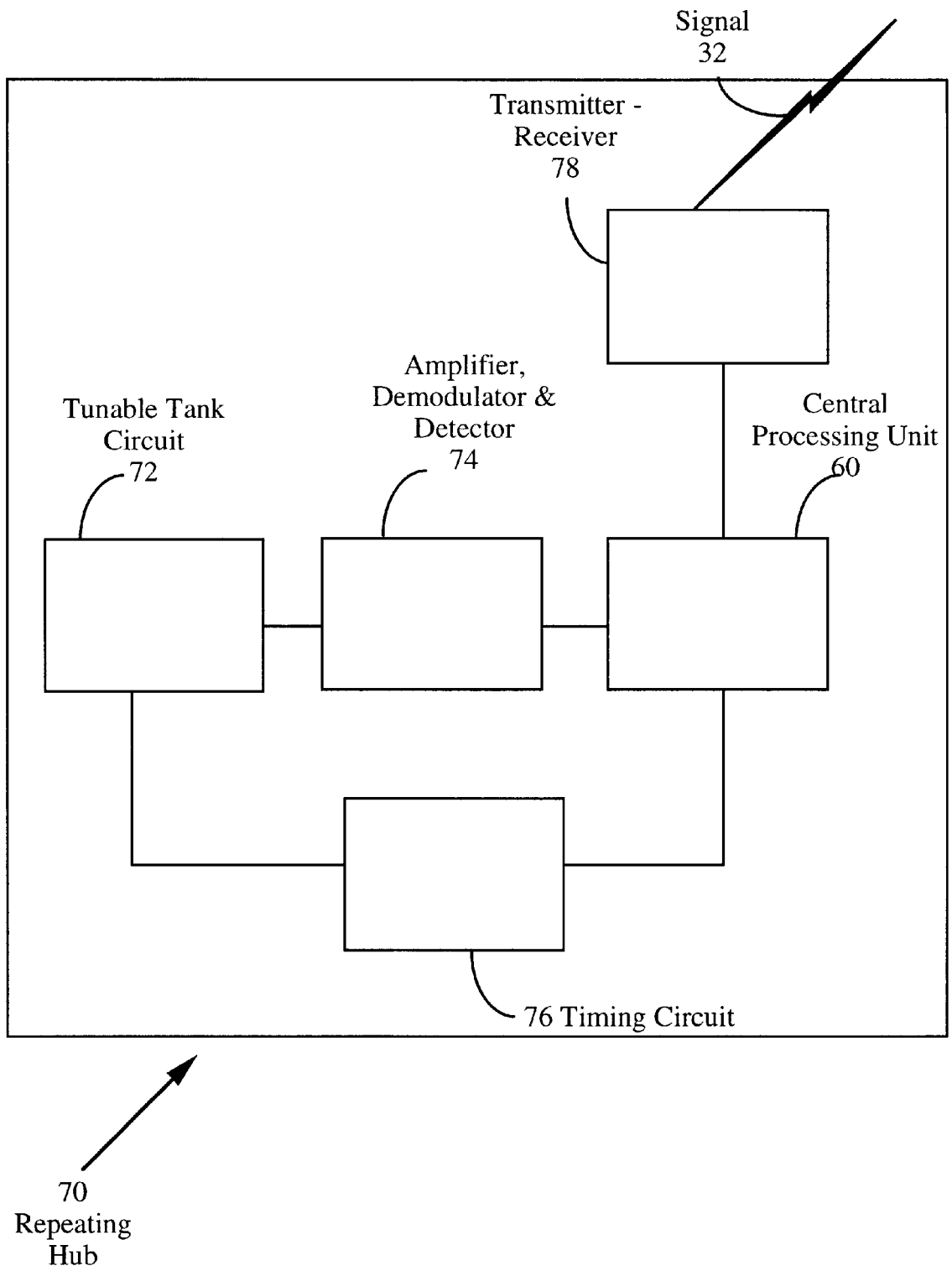
FIG. 3 is a diagram of the repeating hub.

FIG. 3 shows a diagram of the repeating hub 70, wherein a tunable tank circuit 72 sends radio frequency signals (RF) to an amplifier, demodulator and detector 74, which sends a direct current signal (DC) to the Central Processing Unit (CPU) 60. The CPU 60 preferably includes a means of data storage 62. Timing signals are sent by a timing circuit 76 to the tank circuit 72, and to the CPU 60.

A combination transmitter/receiver 78 periodically sends a signal from the repeating hub 70 to an external CPU 60, where the signal is monitored and appropriate action may be taken to ensure the safety and well-being of the user within the selected environment 50.

The signal from the transmitter/receiver 78 may be sent over wires, fiber optic cable, by radio waves to a remote receiver, by ultrasonic waves and/or by infrared waves. The data monitored by the sensors 20 preferably includes both physiological measurements from the user, and non-physiological measurements taken from the user's environment.

Physiological measurements may be monitored directly from the user, or may be obtained indirectly through the use of sensors 20. Physiological measurements preferably include at least one of the following: the user's blood pressure, heart rate, body temperature, body weight and blood glucose level.

Non-physiological measurements selected from the user's environment 50 preferably include at least one of the following: room temperature, ammonia from spilled urine, methane from spoiling food, the presence of smoke, the frequency of electrical usage, the frequency of water usage, the temperature of water flowing from a tap located within the selected environment 50, the user's movement within the selected environment 50, and the use of selected appliances 80. Selected appliances preferably include at least one of the following: a toilet, telephone, stove, microwave oven, toaster, oven, refrigerator, freezer, dishwasher, bath, shower, garbage disposal means, clothes washer, clothes drier, mail box, door and vehicle. Other known appliances may be selected in accordance with the user's activities, and such other appliances are intended to fall within the teaching of this disclosure, and within the scope of the following claims.

A variety of sensors 20 may be used to monitor the activity of the user within the selected environment 50. Preferably, sensors 20 will be selected from at least one of the following: a reed switch, a plunger switch, a pressure sensitive mat, a thermistor, a photo-resistor, a voltage sensitive relay, a smoke detector, a motion detector, a blood pressure monitor, a heart rate monitor, and a weight measuring means. Other known sensors 20 may be used to suite the activities of the user, within the selected environment.

Figure 4:
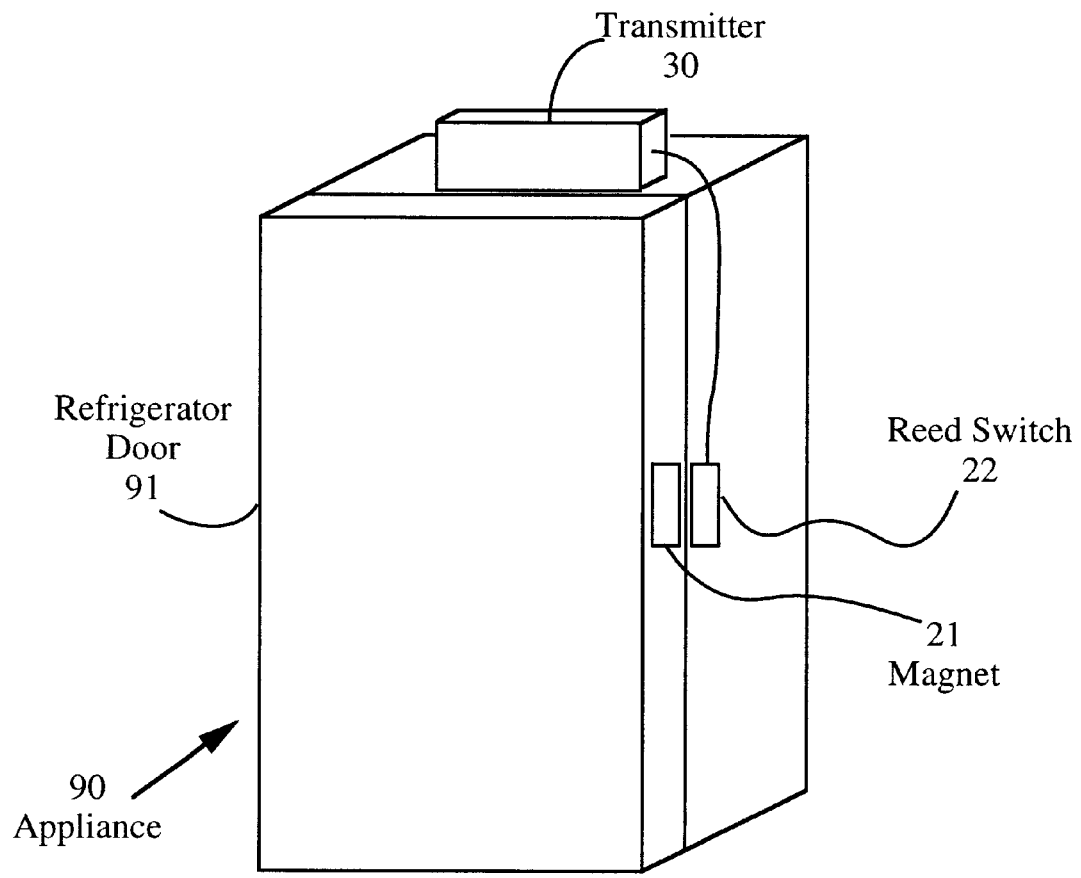
FIG. 4 is a perspective view of a sensor used to monitor a refrigerator door.

As shown in FIG. 4, a sensor 20, in the form of a magnet 21 and reed switch 22, are installed to monitor the use of an appliance 90, such as a refrigerator door 90. A signal from the reed switch 22 is sent to a transmitter 30, which forwards the signal to a multichannel receiver 40, or to the CPU 60. Reed switches 22 are commercially available in either open or closed configurations, to suit the intended appliance 90, and their installation and use is well known in the art.

Any appliance 90 having a door may be monitored in this manner. Examples of appliances which may be monitored, include, but are not limited to the following: refrigerator, freezer, microwave oven, dishwasher, clothes washer, clothes drier, mail box, toaster oven, garage door, inside and outside dwelling doors, cabinet drawers, dresser doors, closet doors, bathroom doors, etc.

Figure 5:
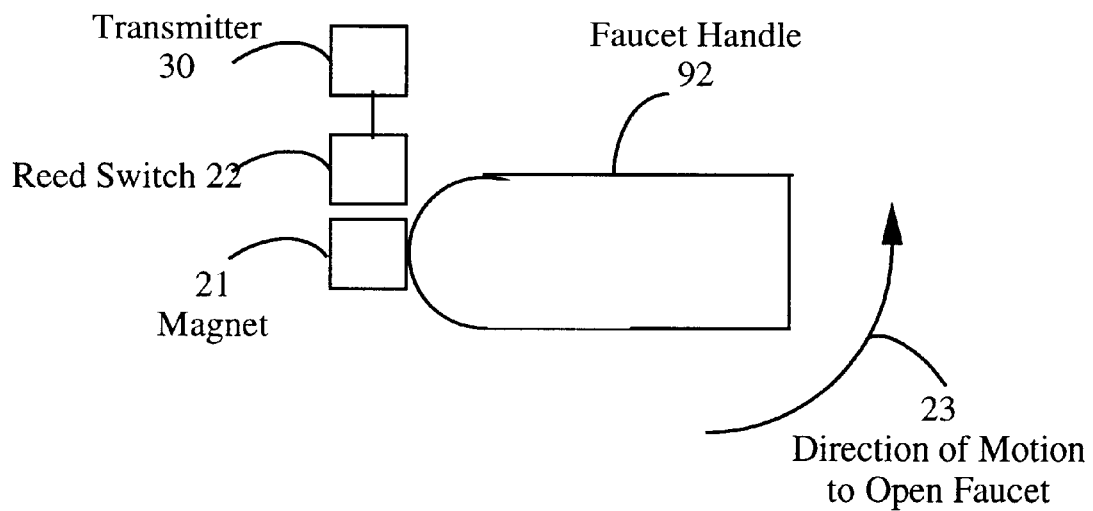
FIG. 5 is a diagram showing a magnetic reed switch used as a position sensor to monitor the position of a water valve.

FIG. 5 shows a reed switch 22 and magnet 21 used to monitor the use of a water tap, typically found adjacent to the kitchen sink, bathroom sink, bathtub or shower. The magnet is preferably mounted on the water tap, and the reed switch 22 is secured to the sink or tub so that no wires need to move when the handle 92 is turned between "on" and "off" positions, as indicated by arrow 23. The condition of the reed switch 22 is sent by the transmitter to the CPU 60 as previously disclosed.

Figure 6:
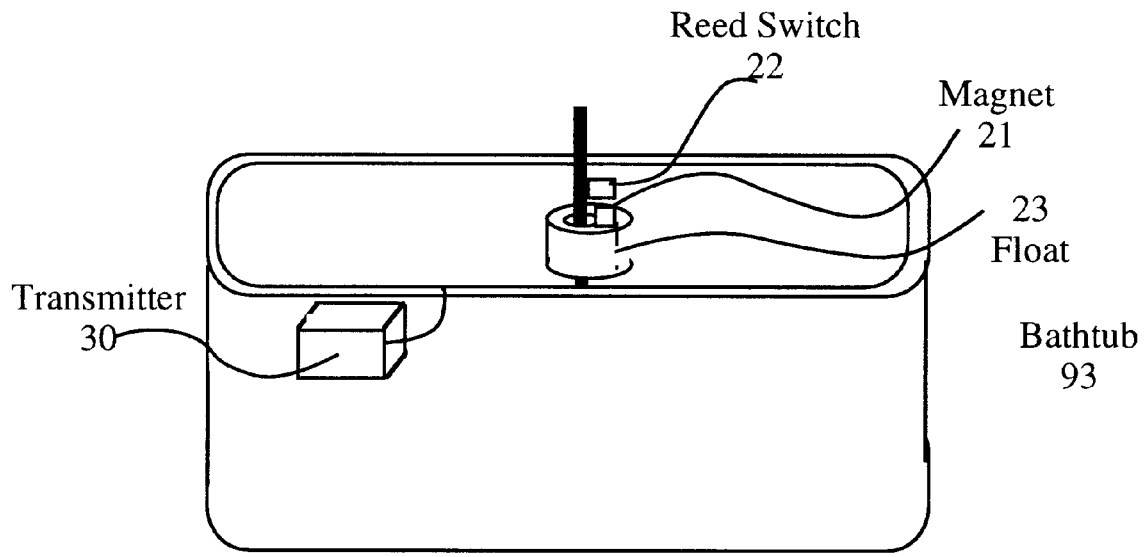
FIG. 6 is a diagram showing a sensor for monitoring the level of water in a bathtub.

FIG. 6 discloses a float 23 used to monitor the level of water in a bathtub. A magnet 21 is preferably placed on the moving float 23, and a reed switch 22 is secured in a manner to monitor the position of the magnet, to indicate when the bathtub is "full" and "not full". A transmitter 30 is used to send the appropriate signal from the reed switch to the CPU 60.

Figure 7:
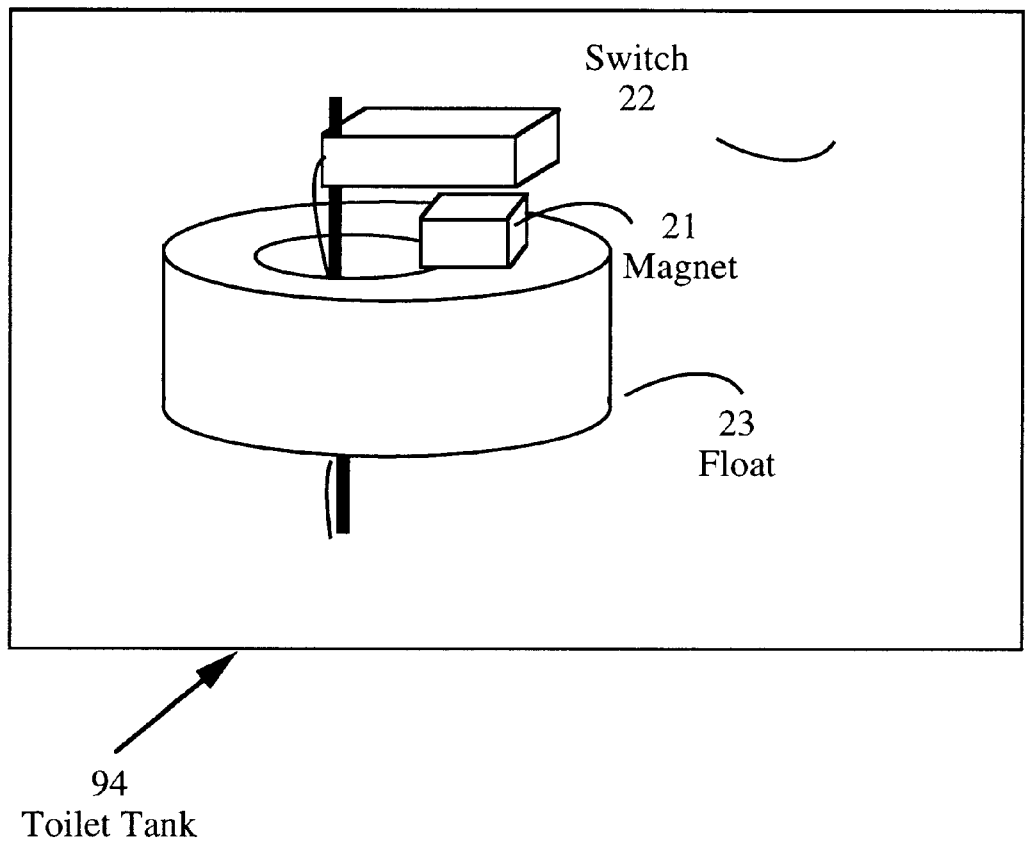
FIG. 7 is a diagram showing a sensor for monitoring the level of water in a toilet bowl.

As shown in FIG. 7, a float 23 may also be used to monitor the level of liquid in a toilet 94. The position of the magnet 21 on the float 23 in relation to the reed switch 22, indicates when the toilet is "full" and is ready to be flushed.

Figure 8:
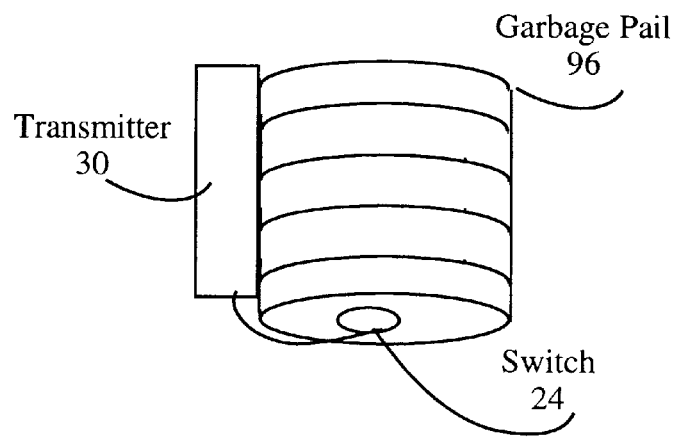
FIG. 8 is a diagram showing a plunger switch used to monitor the use of a garbage pail.

FIG. 8 is representative of a garbage pail 96, wherein a plunger switch 24 is used to indicate when a garbage pail is picked up, or turned over. The plunger switch 24 includes a rod which is held in an extended position by a spring. The plunger switch 24 is preferably mounted on the bottom or side of the garbage pail 96, so that the rod is released when the garbage pail is picked up or tipped over. A transmitter 30 sends a signal to the CPU when the rod is extended. Plunger switches are commercially available and well known in the art, and thus are not further detailed herein.

Figure 9:
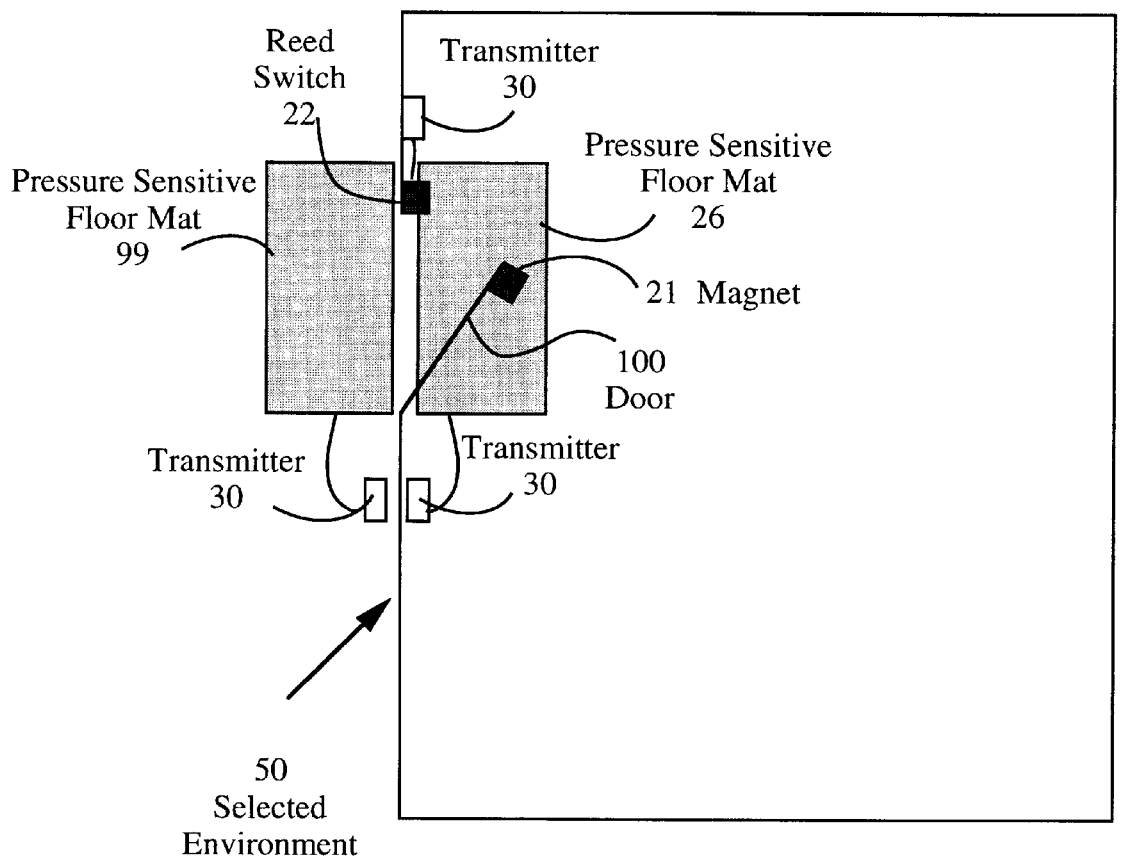
FIG. 9 is a diagram showing the use of sensors to monitor the location of a user in relation to an access door located within the selected environment.

FIG. 9 discloses an example embodiment of several sensors 20 used to monitor a door 100. The combination of sensors 20 can be used to determine whether the user has entered through a door, left through the door, opened the door from the inside and left without closing the door, returned from the outside and entered through the door without closing the door, opened the door from the inside and gone out without closing the door and then returned and closed the door or opened the door from the outside and come in without closing the door, or exited and closed the door.

A reed switch 22 and magnet 21 serve to monitor the condition of the door 100 between open and closed positions. A first pressure sensitive mat 98 is installed inside the door, and a second pressure sensitive mat 99 is installed outside the door. The pressure sensitive mats 98, 99 and the reed switch 22 are connected to respective transmitters 30 to signal the CPU when they are actuated by the user. The pressure sensitive mats are preferably distributed switches, which are normally open, but close when a user steps on them. Pressure sensitive mats are well known in the art, and thus are not further detailed herein.

Where more than one user is present in the selected environment 50, this combination of sensors 20 is particularly useful to determine if more than one user has entered or left the selected environment during the opening and closing of a door 100.

Figure 10:
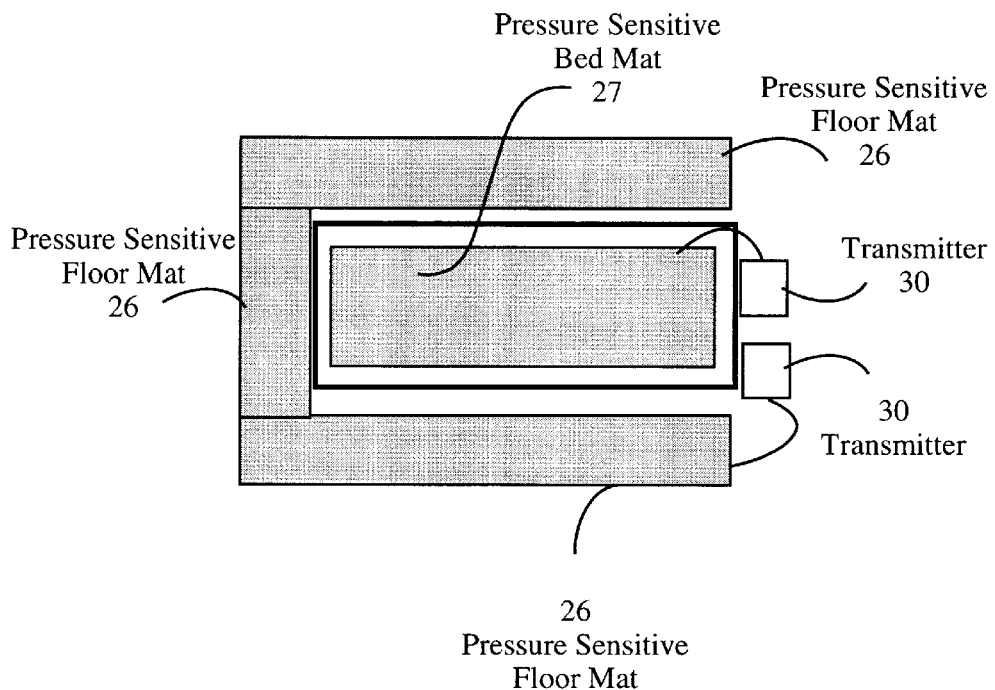
FIG. 10 is a diagram showing the use of sensors in relation to a bed or chair to monitor the activity of the user within the selected environment.

FIG. 10 is representative of the use of several sensors 20 used to determine whether a person has arisen from a bed or chair, or upon arising from the bed or chair, has fallen, and remains motionless, as in the case of a heart attack or stroke. A pressure sensitive mat 27 is placed on the bed or chair, to signal the presence of a user upon the bed or chair. One or more pressure sensitive floor mats 26 are positioned about the bed or chair to signal when the user steps from the bed or chair. If the user falls, and remains motionless for a period of time, the signal from the pressure sensitive floor mat will signal this condition to the CPU 60 over the transmitter 30.

Figure 11:
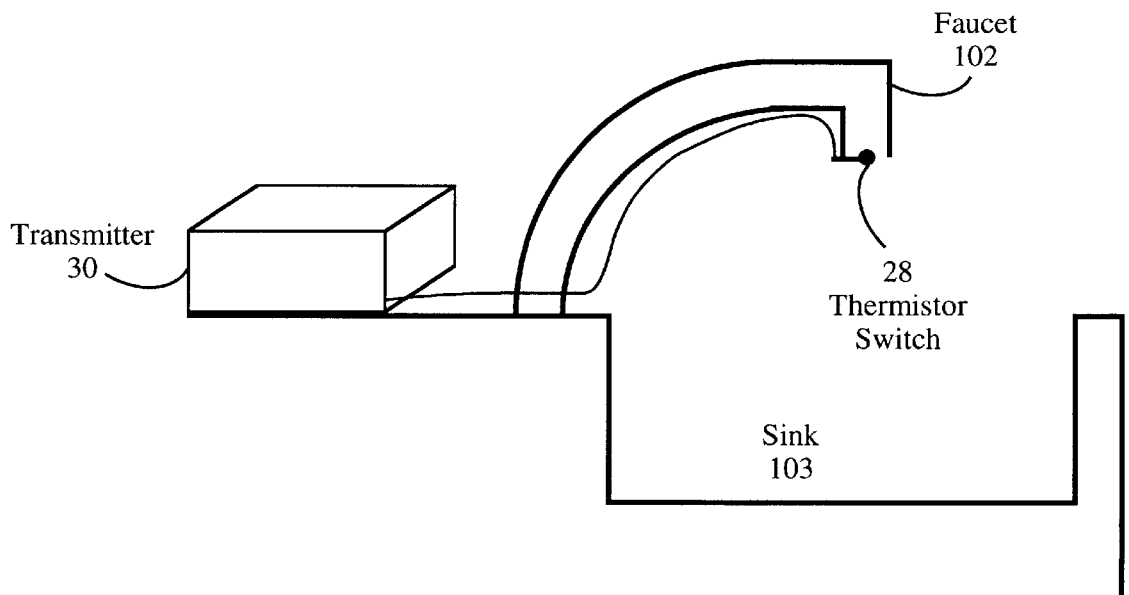
FIG. 11 is a diagram showing the use of a thermistor for monitoring the water temperature and use of a faucet within the selected environment.
Figure 12:
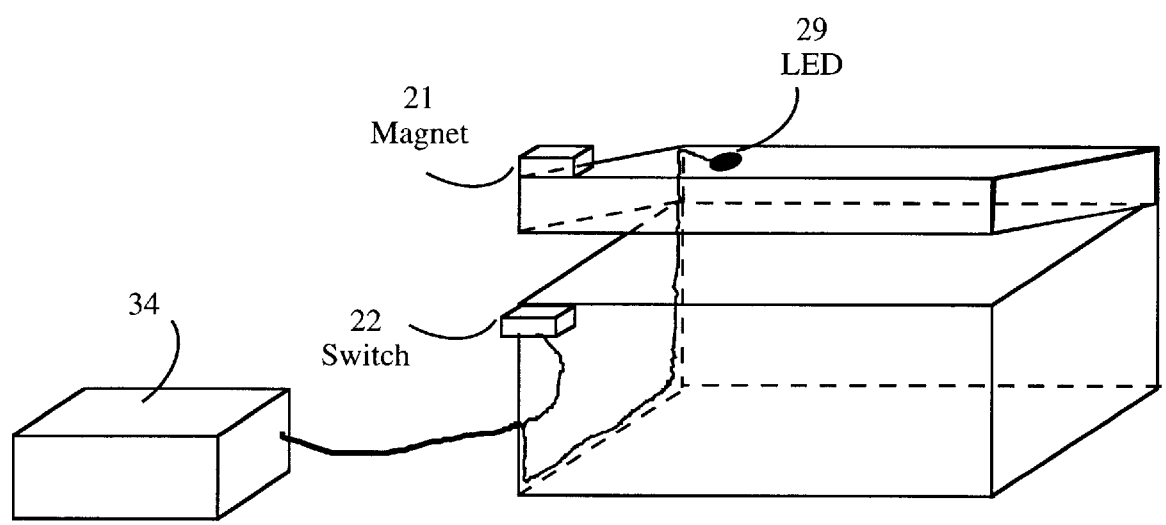
FIG. 12 is a diagram showing the use of a magnet and reed switch and a transmitter/receiver to monitor the use of a pill box or medicine cabinet.

FIG. 11 shows a water faucet 102 fitted with a thermistor 28 for monitoring the temperature of the water coming from the water faucet 102. The thermistor 28 is preferably placed inside the faucet 102 fixture, so that it does not interfere with the operation of the faucet 102. The thermistor 28 changes its electrical resistance in response to the temperature of the water, or air within the faucet 102, and a signal responsive to the change in electrical resistance is sent by transmitter 30 to the CPU 60. The thermistor 28 may be placed in a any suitable faucet 102, such as used in a sink 103, bathtub, or shower head. Thermistors are commercially available, and their installation and use is well known in the are, and thus is not further detailed herein.

Figure 13:
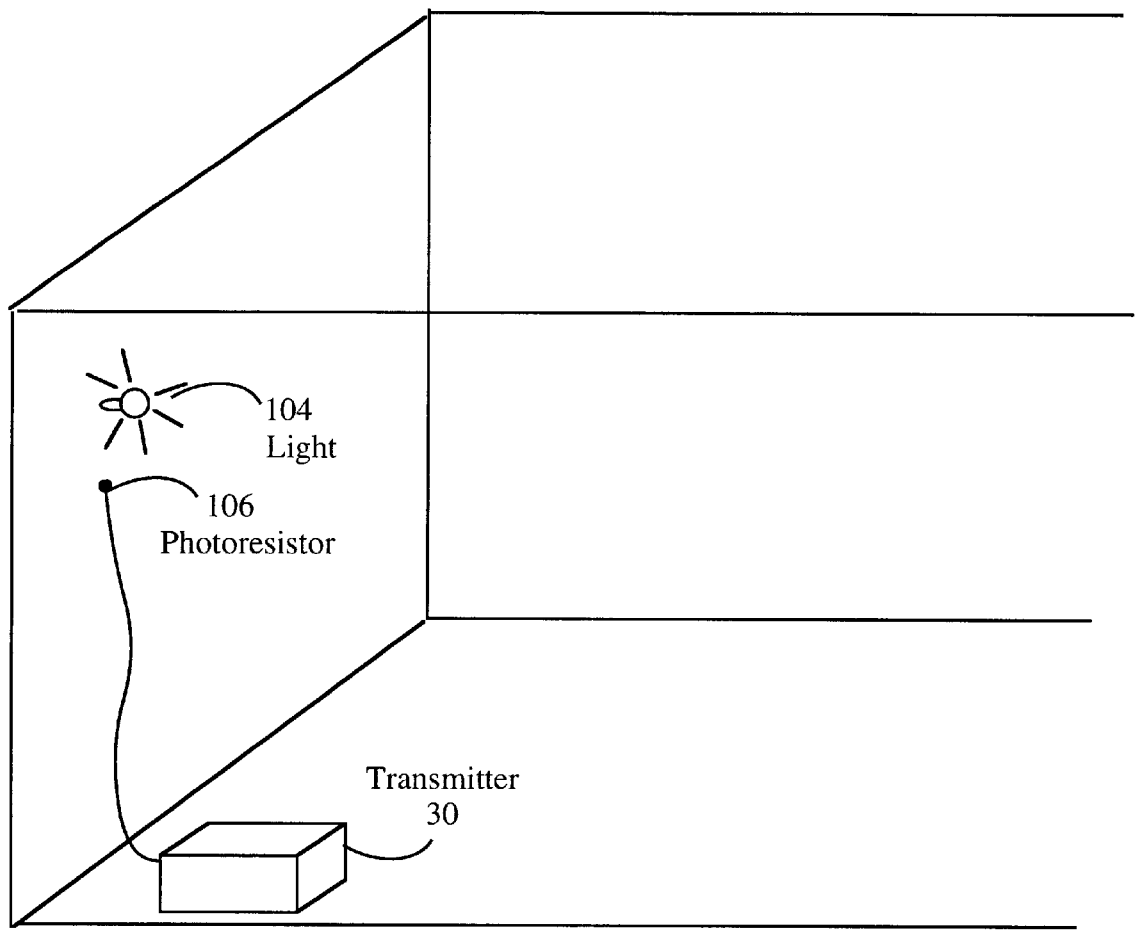
FIG. 13 is a diagram showing the use of a photo resistor sensor to monitor the use of an electric light.

FIG. 13 discloses the use of a photo-resistor 106 to monitor the use of an electric light 104 located within the selected environment 50. The photo-resistor 106 changes its electrical resistance in response to the amount of visible light falling on it. When the light 104 is actuated, the resistance of the photo-resistor 106 lies above a known threshold. When the light 104 is turned off, only ambient light falls on the photo-resistor 106 and its resistance lies below the known threshold. Thus the resistance of the photo-resistor 106 is responsive to the "on" "off" condition of the light 104, and a suitable signal is sent by the transmitter to the CPU 60.

Thus, the "on" "off" condition of the light 104 may be monitored without accessing the light 104 wiring, which may be within a wall or light fixture, or otherwise unaccessible. Photo-resistors 106 are commercially available, and their installation and use is well known in the art, and thus will not be further disclosed herein.

Figure 14:
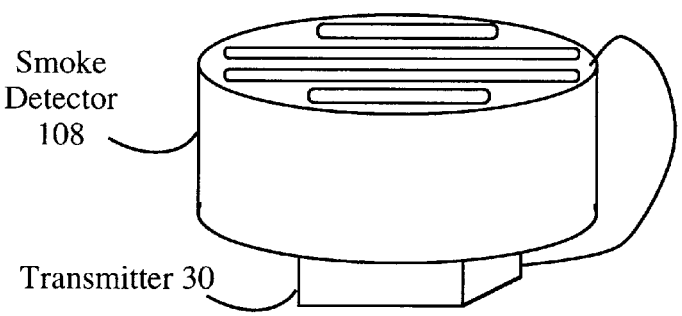
FIG. 14 is a diagram showing the use of a transmitter to monitor the output of a smoke detector.

FIG. 14 is representative of a commercial smoke detector 108, which has been modified to include a transmitter 30 connected to the audible alarm of the smoke detector 108, so that the transmitter 30 is energized when the audible alarm is actuated. Smoke detectors are commercially available, and their installation and use are well known in the art, and thus will not be further detailed herein.

Figure 15:
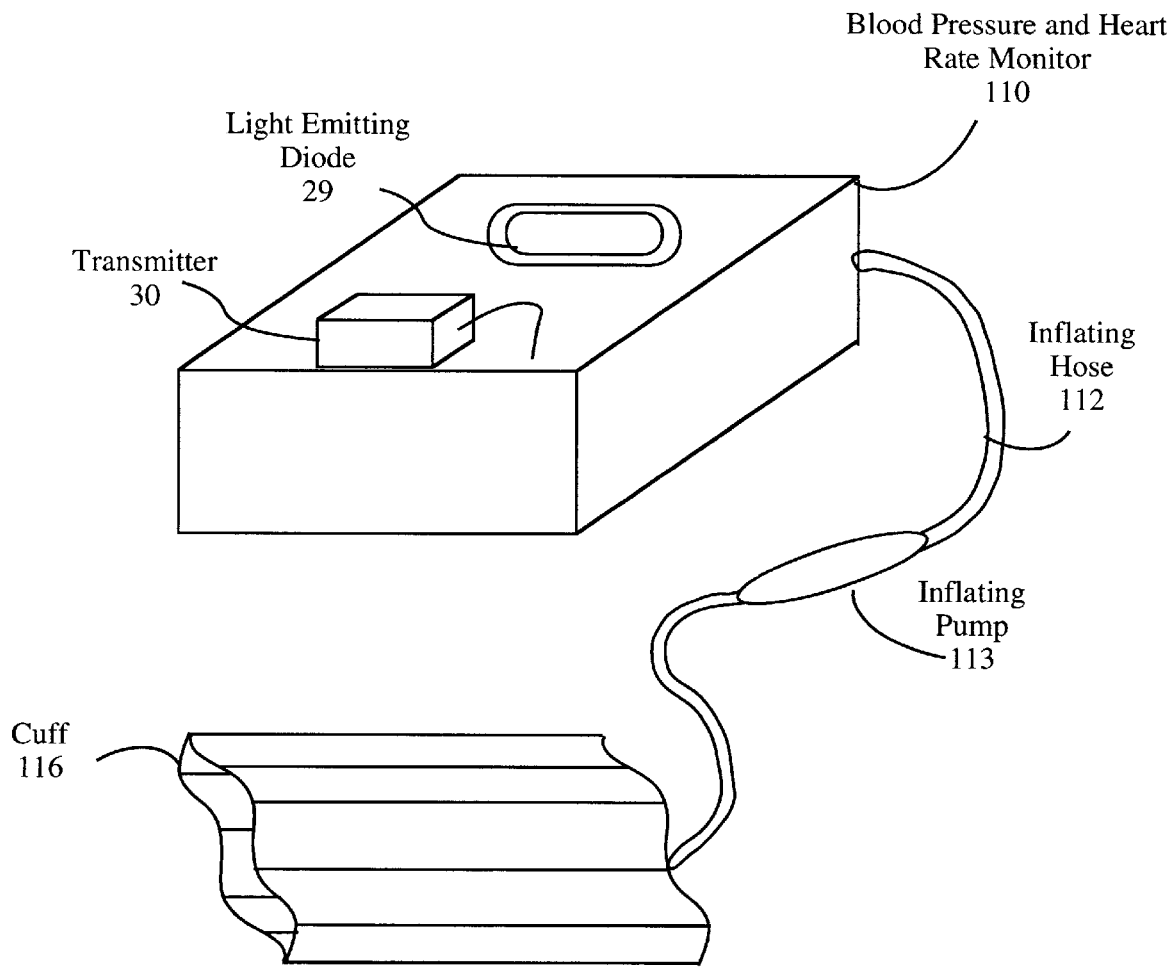
FIG. 15 is a perspective view of a combination blood pressure, heart rate monitor and transmitter for use by a user within the selected environment.

FIG. 15 is representative of a home blood pressure/heart rate monitor 110, which are commercially available without prescription from pharmacies and medical supply stores. The monitor 110 is modified to signal physiological data obtained from its use, by transmitter 30 to the CPU 60. The monitor 110 typically includes a light emitting diode (LED) display 29, a fluid hose 112 connected to a hand pump 114 to inflate a cuff 116 which is inserted over the user's arm to periodically monitor the user's pulse, heart rate and blood pressure.

Data collected by the monitor 110 is sent by transmitter 30 to the CPU, and may be later reviewed by the user, or remotely monitored and reviewed by a doctor, nurse or other person.

The transmitter 30 may be a serial device, which sends a series of digits representative of the data collected, or may be a parallel device, comprising several separate transmitters 30, with each transmitter 30 sending a single digit to the CPU 60.

Other physiological data may be monitored and sent by transmitter 30 to the CPU 60. For example, bathroom scales may be monitored to provide data relevant to the user's weight. Thermometers may be monitored to provide data relevant to the user's body temperature. Likewise, other commercially available consumer medical apparatus may also be monitored, and the data obtained sent by transmitter to the CPU for inclusion in the user monitor 10.

It is well within the scope of this disclosure, that one of average skill in this art, may attach a transmitter to a variety of such commercially available devices to provide data to the CPU for inclusion with this user monitor 10. Such adaptations are intended to fall within the teachings of this disclosure, and are intended to fall within the scope of the following claims.

Figure 16:
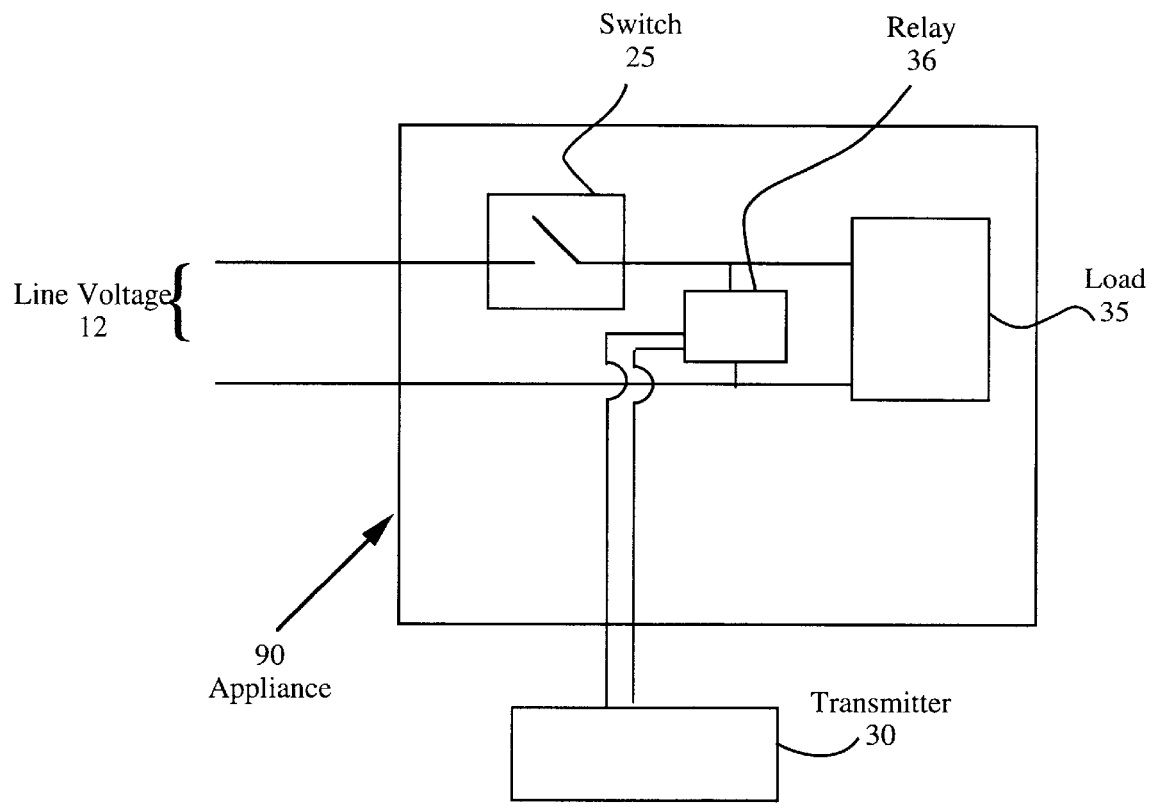
FIG. 16 is a diagram showing the use of a sensor and a transmitter to monitor the use of a selected appliance.

Referring now to FIG. 16, an appliance 90, such as an electric toaster, toaster oven, garbage disposal unit, stove or oven, may be monitored by the user monitor 10. A relay 36 is connected across the load 35 between the switch 25 and the load 35. When the appliance 90 is actuated by switch 25, the line voltage 12 passes through the relay 36, which provides a signal, similar to the reed switch 22 previously disclosed. A signal from the relay 36 is sent by transmitter 30 to the CPU 60, without modifying the appliance 90 switch 25 in any way. Suitable relays 36 are commercially available, and their installation and use are well known in the art, and are thus not further disclosed herein.

Figure 17:
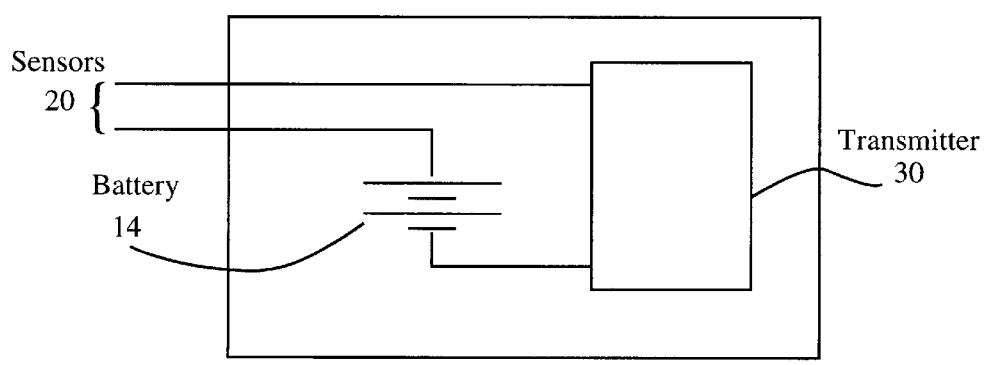
FIG. 17 is a diagram showing the use of a transmitter controlled by a sensor positioned externally to the selected environment.

FIG. 17 is representative of a transmitter 30, which may be a radio transmitter, an ultrasonic transmitter, a laser transmitter connected to a fiber optic cable, or an infrared transmitter. The transmitter 30 is supplied by a power source, such as a battery source 14 shown in FIG. 17. Alternately, a remote electrical power source 12, may be used.

Any of the above referenced sensors 20 may be placed in series between the power source and the transmitter 30, to control the actuation of the transmitter 30. For example, a normally open reed switch 22 is positioned on a refrigerator door 91. The reed switch 22 is open when the refrigerator door 91 is closed, and the transmitter 30 will be inactive. When the refrigerator door is opened, the reed switch 22 will close, sending power to the transmitter 30 from the battery 14 or other power source. The transmitter 30 will then send a signal to the CPU 60. This minimizes power consumption by placing the transmitter in the "off" condition when the sensor 20 is inactive.

The thermistor switch 28 shown in FIG. 11 and the photo-resistor switch 106 shown in FIG. 13 do not have zero resistance in one state, and infinite resistance in another state, as do the reed switches 22 shown in FIG. 4 through 7 and plunger switch shown in FIG. 8.

Instead, photo-resistor switches 106 and thermistor switches 28 vary their resistance between high and low values. Typically, the high value is 12 ohms and the low value is 5 K ohms. The transmitter 30 of FIG. 17 may still be used with these values if the voltage source is chosen correctly, such that the voltage required to drive the transmitter appears on its terminals even after dropping through the variable resistor.

Devices, such as the smoke detector 108 shown in FIG. 14, can use the transmitter 30 shown in FIG. 17, by removing the transmitter's internal battery 14. The result is a transmitter which has no internal power supply but depends on the power supply of the external device.

Figure 18:
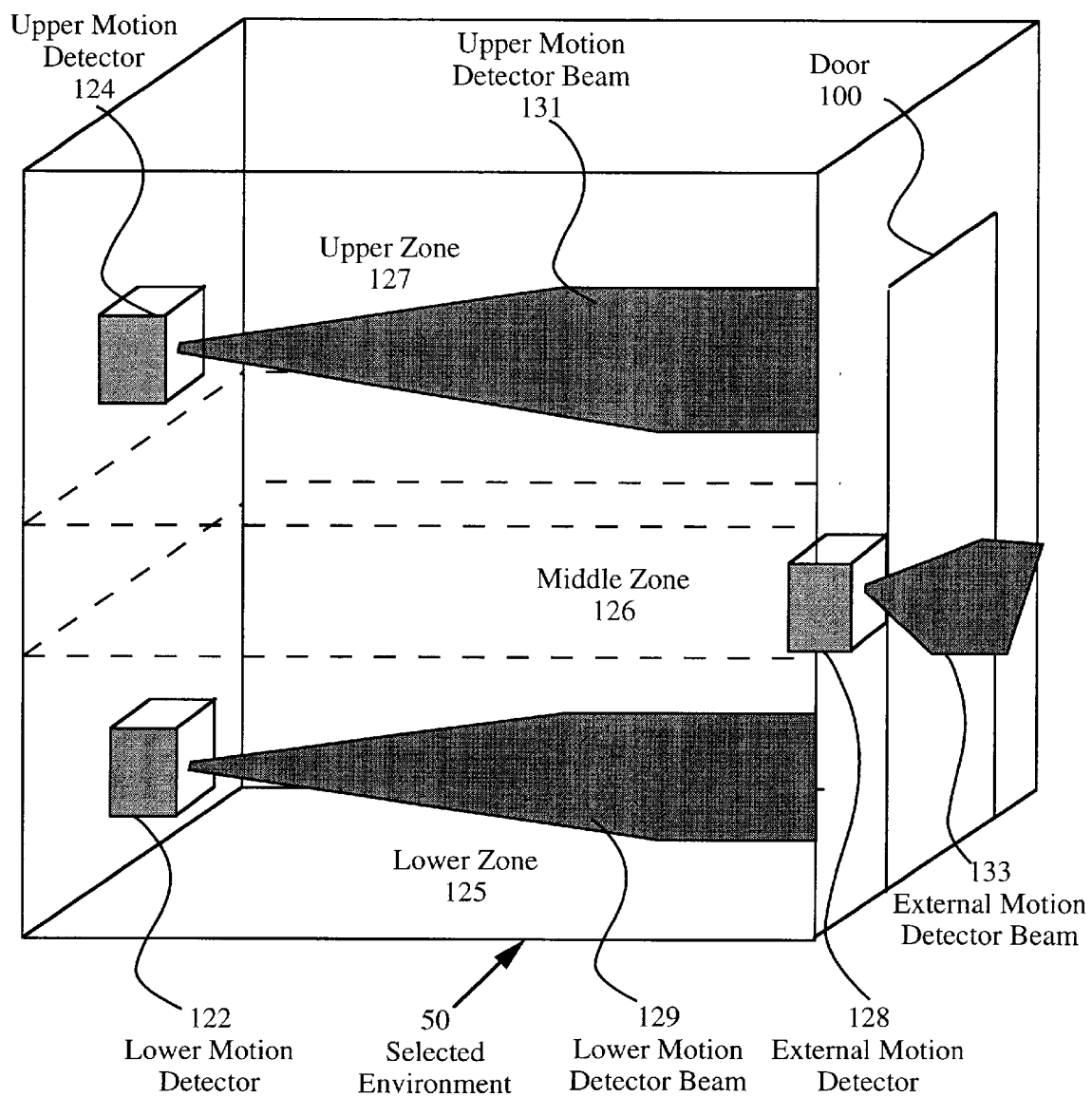
FIG. 18 is a diagram of upper and lower motion detectors used as a fall detector within the selected environment.

FIG. 18 discloses a fall detector 120, comprising a lower motion detector 122 and an upper motion detector 124. The motion detectors 122, 124 may be passive or active infrared detectors, passive or active ultrasonic detectors, or active microwave detectors. Such motion detectors 122, 124 are commercially available, and thus their installation and operation are not further detailed herein.

The motion detectors 122, 124 are positioned to detect motion within a selected environment 50, such as a single room 52. The room 52 is divided horizontally into three zones, a lower zone 125, a middle zone 126 and an upper zone 127. The lower zone 125 extends from the floor to about knee height on a typical user, or from eighteen inches to twenty-four inches above the floor. The lower motion detector 122 is positioned to send a beam 129 to detect movement only in the lower zone 125.

The middle zone 126 extends from the upper portion of the lower zone 125 to about waist height on a typical user, or from eighteen to twenty-four inches above the floor to thirty to forty-eight inches above the floor.

The upper zone 126 extends from the upper portion of the middle zone 125, or from thirty to forty-eight inches above the floor to at least six feet above the floor and preferably to the ceiling of the selected environment 50. The upper motion detector 124 is positioned to send a beam 131 to detect movement only in the upper zone 127.

Multiple motion detectors 122 or 124 in the same zone may be connected in parallel, so that they in effect form a single motion detector. The motion detectors 122 in the lower zone 125 are connected to a suitable transmitter 30. Alternately, the motion detectors 122 in the lower zone 125 may be each connected to separate transmitters 30, thus forming a position sensitive burglar alarm.

Motion detectors 124 in the upper zone 126 may be connected to a suitable transmitter 30. Alternately, the motion detectors 124 in the upper zone 127 may each be connected to separate transmitters 30.

When a user is located by both the upper and lower motion detectors 122, 124 in the upper zone 127 and the lower zone 125 in the selected environment 50, no fall has occurred. However, when the user is located by the lower motion detector 122 and not the upper motion detector 124, it is likely a fall has occurred. In this case, an alarm may be actuated by the CPU.

If all motion then ceases in both the upper and lower zones 125, 127 as noted by the upper and lower motion detectors 124, 122, then the fall may be serious and a suitable alarm 64 is preferably actuated by the CPU 60.

An external motion detector 128 is preferably mounted adjacent to each of the doorways 100 leading away from the room 52 where the fall detector 120 is installed. These external motion detectors 128 are aligned so that they detect a user in an adjacent room, and also serve to detect users leaving the room where the fall detector 120 is installed. Where adjoining rooms have fall detectors 120 installed, or external motion detectors 128, the data from each of the fall detectors 120 or motion detectors 128 may be combined. The fall detector 120 in one room may be disabled when a user is in an adjacent room.

Upper motion detectors 124 may be placed on opposite sides of a room to enable the motion detectors 124 to detect movement of the user's hands. Preferably, the upper motion detector 124 is positioned to view the tops of tables and counters where activities such as food preparation and card playing occur.

Figure 19:
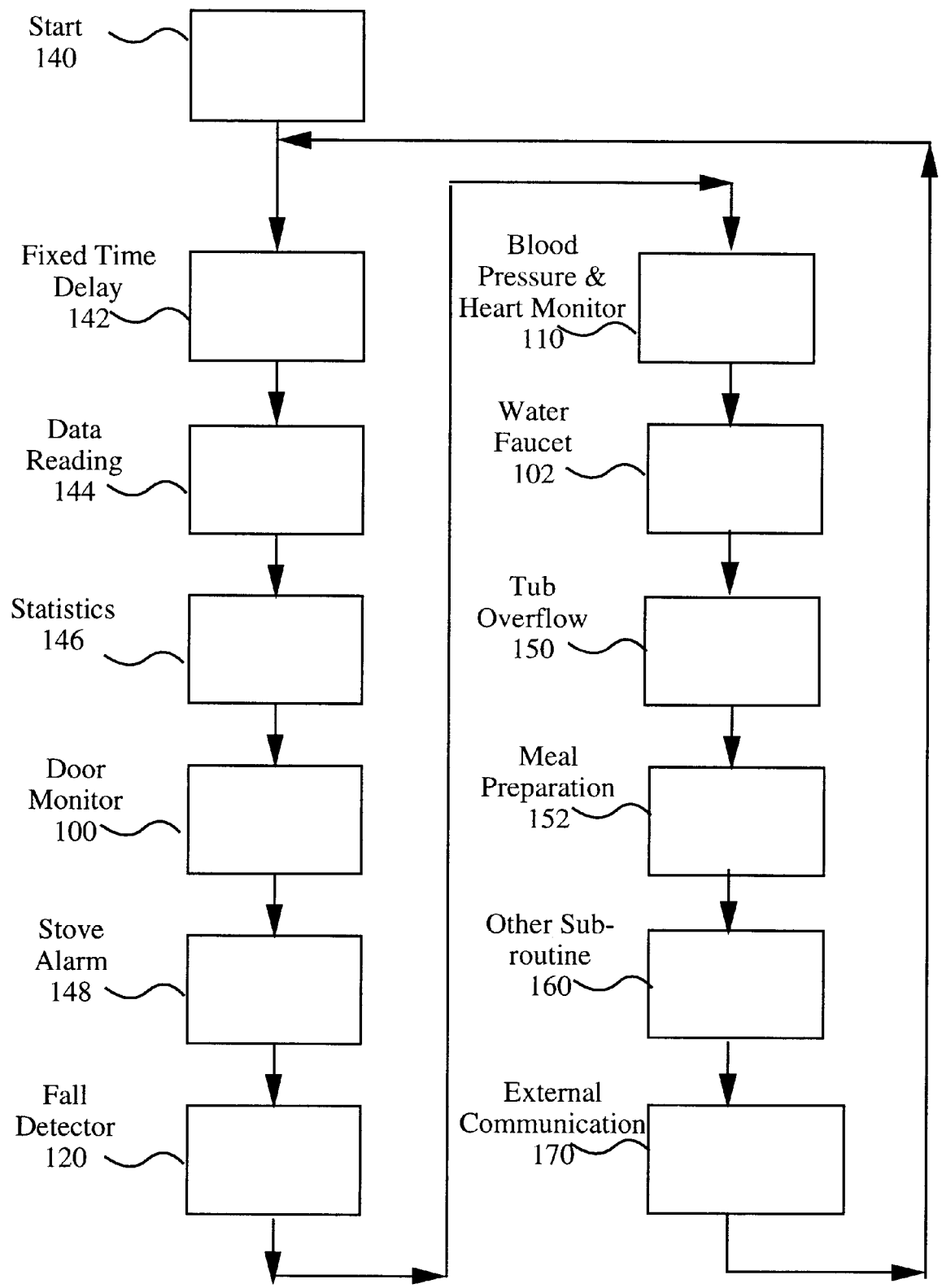
FIG. 19 is a flow chart showing the method for monitoring the user within the selected environment.

FIG. 19 shows several reed switch sensors 22 operatively connected to a plug-in board having I/O ports installed in the central processing hub. The sensors 20 are connected by circuitry or wires. Preferably a common ground is connected to these sensors 20. Alternately, separate ground connections may be made for each sensor 20.

Since the reed switch sensors 22 do not produce a voltage to drive the I/O board, one must be supplied. FIG. 19 discloses a means for providing power to multiple reed switch sensors 22 using a common 12 volt DC power supply. Each sensor is represented by a separate reed switch 22. The voltage on the I/O input port is zero when the reed switch 22 is closed, as the reed switch 22 shorts the input to ground. The resistors R1 and R2 are chosen so that the voltage on the I/O input port is +5 volts when the reed switch 22 is open. This occurs when:

$$R2/(R1+R2)*12=5$$

R1 and R2 must be chosen to be large enough to limit the current drawn by the power supply to an acceptable value. The current drawn by N sensors is:

$$I_{ps}=12/(R1+R2)*N$$

when N reed switches 22 are open, neglecting the current drawn by the I/O port itself. Knowledge of the power supply limit current and the number of sensors allows calculation of an upper limit on Ips, and hence on a lower limit on (R1+R2). This limit, combined with equation 1 allows calculation of R1 and R2 separately.

In order to ensure that the current drawn by the I/P port is negligible, the following inequality must hold, where R I/O is the impedance of the I/O port:

$$(R1*R2)/(R1+R2) R\ I/O.$$

If the values of R1 and R2 calculated above do not satisfy this inequality, then a power supply with greater current capacity or an I/O port with a greater impedance must be chosen.

Several sensors connected to a plug-in board with I/O ports installed in the central processing hub. The details of the transmitter are shown in FIG. 17. The receiver is a radio wave receiver, which contains a tank circuit tuned to the transmitter's radio frequency and having a high enough Q that the frequency is not affected by the other radio transmitters in the User Monitor 10.

The radio waves emitted by the transmitter need not be modulated, other than being turned on and off. In this case no demodulation stage is required in the receiver and the amplified RF energy can be detected, limited to 5 volts maximum and applied to the I/O port.

If protection against interference is desired then the carrier can be modulated at a suitable audio frequency. Either frequency modulation (FM) or amplitude modulation (AM) may be employed. In either case, the receiver is tuned to the transmitter's carrier frequency, and the modulation is recovered by standard means, amplified in an audio amplifier, detected and applied to the I/O port.

Where infrared or ultrasonic transmission is preferred over the radio transmission disclosed herein, it is believed that the disclosed invention may be adapted by one skilled in this art to either infrared or ultrasonic transmission. Therefore, such adaptation is intended to be included within the scope of this disclosure.

FIG. 19 shows a flow chart for a computer program to implement these functions. The program begins when the user, or others, enter a number of parameters specific to the user being monitored. These parameters may include the time at which the person ordinarily eats breakfast, lunch and dinner, when they usually arise in the morning and when they usually go to bed in the evening.

The program enters an endless loop. The time delay subroutine introduces a fixed time delay so that the activities in the loop repeat at regular or nearly regular intervals. A sampling interval near 0.1 seconds is satisfactory. A sampling interval selected from 0.01 seconds to 10.0 seconds is preferred. The data reading subroutine samples the digital I/O lines and the A/D converters, if any, and records each sample in an appropriate location in memory.

The statistics subroutine determines the change in each value taken from the digital I/O lines since the last sample was taken. It records the change in an appropriate location in memory. If the change means that the door, water tap, motion detector or other device has been turned on, then the subroutine notes the time and associates the time with the change. If the change means that the device has been turned off, then the subroutine determines the time interval since the device was turned on and calculates an updated mean and variance for that device's on time.

The door monitor subroutine determines if a user has just entered a room 52 where the User Monitor 10 is installed. It also determines if the user left the monitored room 52 and closed the door 100, looked into the monitored room without closing the door 100, or looked out of the monitored room without closing the door 100. The User Monitor 10 makes these decisions based on current and previously collected data.

The door monitor subroutine uses data from sensors, similar to those shown in FIG. 9. The door monitor subroutine includes a door position switch 25 and pressure sensing floor mats 98, 99 located on each side of the door. Alternately, a motion detector or an infrared or ultrasonic beam positioned to be interrupted when a user stands inside or outside the door could be used in place of the pressure sensing floor mats 98, 99.

Referring now to the door monitor subroutine, when the door status changes from "closed" to "open", the door monitor subroutine notes the value of the floor mat for persons within the door. If this value is "on" then a person is inside the door. If this value is "off", then no one is inside the door.

When the door status changes from "open" to "closed", the door monitor subroutine again notes the value of the floor mats. The data from the sensors 20 is entered into a truth table similar to that shown in FIG. 20, to determine what action just took place.

Next the user code updates its estimate of the number of people with the selected environment 50. When a user enters the selected environment 50, the user code is updated by "1". If a user leaves the selected environment, the user code is reduced by the "1". In the event that a user opened the door to look in, but did not enter, then the user count remains the same. If a user opens the door to look out, but does not leave the selected environment, then the user count also remains the same.

The user code preferably includes a timer which actuates an alarm if the door is left open beyond a preset time, either with or without the presence of a user in the selected environment. The preset time may be set at the time the User Monitor 10 is installed, or may be changed by an authorized external user via signals on the telephone line. There may be two or more preset times, if desired, to allow for a warning of an open door, wherein a shorter preset time may be authorized late at night, and a longer preset time authorized during daylight hours.

Separate alarms may be actuated when the user leaves or enters through the opened door. Thus, the location of the user may be signaled to others, or the presence of more than one person may be monitored in the controlled environment.

The stove warning subroutine examines the status of the stove burner, and the time in which the burner was turned on. If the burner is on, the User Monitor 10 determines how long the burner has been on, and compares that time to a threshold time entered at the time the User Monitor 10 was installed. There may be multiple threshold times, corresponding to the time of day and to whether a person is within the selected environment.

If the stove burner has been on longer than the threshold time, then the User Monitoring Means 10 will issue an alarm. If a user is within the selected environment, then the User Monitoring Means 10 will first emit an audible and/or visual alarm, for the benefit of the user. If the user does not respond by turning off the stove burner or pressing a reset button after a predetermined time interval, then the User Monitoring Means 10 will issue a further alarm to an external user.

The external user may be a friend, relative, building staff member, or fire department. If the User Monitoring Means 10 determines that no one is within the selected environment, then the User Monitoring Means 10 will issue both alarms at the same time.

The fall detector subroutine examines the status of the upper motion detectors 124 in a room 52 in which the fall detector 120 is installed. The upper motion detector 124 is seeking the cessation of motion on the upper motion detectors. This state will be evidenced by a change in the upper motion detectors 124 output from "on" to "off". When the fall detector finds this condition it notes the clock time and starts a timer for a preset time delay T1.

Time delay T1 accounts for the possibility that the inhabitant may stand or sit so still that the upper motion detectors 124 do not detect the user. An alarm is actuated only after the time T1 has elapsed. The time T1 is set longer than the time that almost everyone sits without moving.

After T1 elapses without motion on the upper motion sensors, the fall detector subroutine examines the lower motion sensor 122. If these sensors are "on", indicating that there is motion in the lower part of the room 52, the fall detector 120 subroutine waits a further delay time T2. Time delay T2 accounts for the possibility that the user's feet or lower legs may move before their upper body moves, such as when swinging the leg before arising from a chair. If no motion occurs in the upper part of the room 52 after the time delay T2, then the fall detector 120 determines that the user has fallen and is struggling to get up, and issues an alarm accordingly.

If the external motion detectors in an adjacent room indicate the presence of a user in the adjacent room, then the fall detector does not signal an alarm. The fall detector assumes that the user in the adjacent room will deal with the fall, and an alarm would only be a distraction to the user coming to the rescue of the fallen user. This feature also prevents false alarms caused by pets who may remain in the room with the fall detector after the user has left, and then move about within the room, setting off the lower motion detector 122, thus mimicking a fallen person.

The fall detector subroutine also cancels the fall alarm if no motion on the lower motion detector 122 takes place for a third time delay T3, following the end of motion on the upper motion detectors 124. This reduces false alarms associated with power surges or other malfunctions that might occur if the fall detector were allowed to run indefinitely.

Delay times T1, T2 and T3 may be entered into the code at startup, or they may be modified from time to time by an external user, communicating with the User Monitoring Means 10 by telephone lines.

Thus, while the User Monitoring Means 10 has been fully described and disclosed, numerous modifications will become apparent to one of ordinary skill in this art, and such adaptations and modifications are intended to be included within the scope of the following claims.

What is claimed is:

1. A method for user monitoring, for monitoring and reporting the condition of a user in a selected environment, which comprises:
   a) a sensing means for monitoring the time and duration of use of each of a plurality of selected elements, selected from at least one of physiological measurements of the user and at least one of non-physiological measurements from the selected environment;
   b) a reporting means for transmitting the data from each of the monitoring means to a central processing unit;
   c) an analyzing means for analyzing the data received by the central processing unit to establish a pattern of user behavior and normal-use parameters for each of the plurality of selected elements being monitored, and for determining potentially dangerous behavior when the normal-use parameters of at least one selected element deviates from the normal-use parameters previously established for that selected element; and
   d) a signaling means selected from at least one of the following: a printing means, a synthesized voice signaling means, a telephone message signal means and a video monitoring means, a visual warning means and an audible warning means, whereby,
   the signaling means is used for signaling beyond the selected environment when at least one selected element deviates from the normal-use parameters being monitored.

2. The method of claim 1, wherein the physiological measurements selected from the user's environment are selected from sensors monitoring at least one of the following: the user's blood pressure, the user's heart rate, the user's body temperature, the user's body weight, and the user's blood glucose level.

3. The method of claim 1, wherein the non-physiological measurements selected from the user's environment are selected from sensors monitoring at least one of the following: room temperature, ammonia from spilled urine, methane from spoiling food, a presence of smoke, frequency and duration of electrical use, frequency and duration of water usage, water temperature flowing from a tap, the user's movement, and the use of selected appliances.

4. The method of claim 3, wherein the use of selected appliances includes sensors for monitoring at least one of the following: a toilet, telephone, stove, microwave oven, toaster, oven, refrigerator, freezer, dishwasher, bath, shower, garbage disposal means, clothes washer, clothes drier, mail box, door, and vehicle.

5. The method of claim 1, wherein at least one motion detector is used for monitoring the time and movement of the user within the selected environment, and to detect the absence of movement and excessive movement which deviates from the normal use parameters established by the analyzing means.

6. The method of claim 1, wherein the signaling means further comprises dialing one or more pre-selected telephone numbers when at least one selected element deviates from the normal use parameters being monitored, and sending a message via telephone to at least one pre-selected telephone number describing the circumstances relating to the deviation of the normal use parameters.

7. The method of claim 1, wherein the sensing means is selected from at least one of the following: a reed switch, a plunger switch, a pressure sensitive mat, a thermistor, a photo-resistor, a voltage sensitive relay, a smoke detector, a motion detector, a blood pressure monitor, a heart rate monitor, and a weight measuring means.

8. The method of claim 7, wherein the motion detector sensing means is selected from at least one of the following: an ultrasonic motion detector, a passive infrared motion detector, an active infrared motion detector, and a microwave motion detector.

9. The method of claim 8, wherein at least one motion detector is positioned within the selected environment for monitoring a lower zone extending from the floor to about two feet above the floor; a middle zone extending from about two feet above the floor to about four feet above the floor; and an upper zone extending from about four feet above the floor to the ceiling.

10. The method of claim 7, wherein the transmitting signal from the sensing means is transmitted via a transmitter powered by electricity over power distribution lines.

11. The method of claim 10, wherein the transmitter is powered by electricity from a battery source located in proximity to the sensing means.

12. The method of claim 1, wherein the selected environment for monitoring is selected from one of the following:

a room, a home, an apartment, an apartment complex, an office, a nursing home and a hospital.

13. The method of claim 1, wherein the repeating hub transmits data in serial fashion in a prearranged sequence to the central processing unit.

14. The method of claim 1, wherein the repeating hub transmits data in parallel fashion on separate data links to the central processing unit.

15. The method of claim 1, wherein the signaling means transmits selected data from the central processing unit to a remote location via at least one data link selected from the following: radio signals, ultrasonic signals, infrared signals, and a hard wired link.

16. The method of claim 15, wherein the hard wired link for transmitting comprises at least one of the following: a fiber optic transmission line, a telephone line, a coaxial cable line, a cable television line, and dedicated electric transmission lines.

17. A method for detecting the position and movement of a user within a selected environment, which comprises:
   a) a first motion detector for detecting at least a portion of a user along a horizontal plane forming a lower zone extending between the floor and a first middle position selected from eighteen inches to twenty-four inches above the floor;
   b) a second motion detector for detecting at least a portion of a user along an upper zone extending in a horizontal plane from a second middle position selected from thirty inches to forty-eight inches above the floor, and extending to an upper position selected from 70 inches to the ceiling of the selected environment; and
   c) a middle zone extending between the first middle position of the lower zone, and the second middle position of the upper zone; and
   d) at least one transmitting means for transmitting the data from a selected motion detector to central processing unit.

18. The method of claim 17, wherein the user monitoring by motion detector is selected from at least one of the following: a passive ultrasonic motion detector, an active ultrasonic motion detector, a passive infrared motion detector, an active infrared motion detector, and an active microwave motion detector.

19. A method of user monitoring, for monitoring and reporting the condition of a user in a selected environment, which comprises:
   a) a monitoring means for monitoring the time, frequency and duration of use of each of a plurality of selected elements, selected from sensors monitoring at least one physiological measurement of the user, comprising the User's blood pressure, the user's heart rate, the user's body temperature, the user's body weight, and the user's blood glucose level; and from sensor's monitoring at least one non-physiological measurement from the selected environment further comprising the room temperature, ammonia from spilled urine, methane from spoiling food, the presence of smoke, water usage, the user's movement, and the use of selected appliances;
   b) a reporting means for transmitting the data from each of the monitoring means to a repeating hub;
   c) a transmitting means for transmitting the data from the repeating hub to a central processing unit;
   d) an analyzing means for analyzing the data received by the central processing unit to establish a pattern of user behavior and normal-use parameters for each of the plurality of selected element; and
   e) a signaling means selected from at least one of the following: a printing means, a synthesized voice signaling means; a telephone message signaling means, and a video monitoring means, whereby
   the signaling means is used for signaling beyond the selected environment when at least one selected element exceeds the normal-use parameters being monitored.

20. The method of claim 19, wherein at least one motion detecting means is used to monitor the time and movement of the user within the selected environment, and to detect the absence of movement and the excessive movement which deviates from the normal use parameters established by the analyzing means.

21. The method of claim 19, wherein the sensing means comprises a pressure sensitive mat positioned at the top and bottom of a plurality of stairs to monitor user falls on stairs.

22. A method of user monitoring, for monitoring and reporting the condition of a user in a selected environment, which comprises:
   a) a monitoring means for monitoring the time, frequency and duration of use of each of a plurality of selected elements, selected from sensors monitoring at least one physiological measurement of the user, comprising the user's blood pressure, the user's heart rate, the user's body temperature, the user's body weight, and the user's blood glucose level; and from sensor's monitoring at least one non-physiological measurement from the selected environment further comprising the room temperature, ammonia from spilled urine, methane from spoiling food, the presence of smoke, water usage, the user's movement, and the use of selected appliances;
   b) a transmitting means for transmitting the data directly from each of the monitoring means to a central processing unit;
   c) an analyzing means for analyzing the data received by the central processing unit to establish a pattern of user behavior and normal-use parameters for each of the plurality of selected element; and
   e) a signaling means selected from at least one of the following: a printing means, a synthesized voice signaling means; a telephone message signaling means, and a video monitoring means, whereby
   the signaling means is used for signaling beyond the selected environment when at least one selected element deviates from the normal-use parameters being monitored.

* * * * *